(12) United States Patent
Obara et al.

(10) Patent No.: US 8,294,122 B2
(45) Date of Patent: Oct. 23, 2012

(54) METHOD FOR FLUORESCENCE ANALYSIS AND FLUORESCENCE ANALYZER

(75) Inventors: Takayuki Obara, Tsuchiura (JP); Satoshi Takahashi, Hitachinaka (JP); Akira Maekawa, Hitachinaka (JP); Takuya Matsui, Mito (JP); Nobutaka Kumazaki, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 714 days.

(21) Appl. No.: 12/400,321

(22) Filed: Mar. 9, 2009

(65) Prior Publication Data

US 2009/0242804 A1    Oct. 1, 2009

(30) Foreign Application Priority Data

Mar. 31, 2008  (JP) ................. 2008-089174

(51) Int. Cl.
   *G01N 21/64*  (2006.01)
(52) U.S. Cl. ............... 250/461.1; 356/301; 356/445
(58) Field of Classification Search ............... 250/461.1; 356/301, 445
   See application file for complete search history.

(56) References Cited

U.S. PATENT DOCUMENTS

| | | | |
|---|---|---|---|
| 7,329,492 B2 | 2/2008 | Hardin et al. | |
| 2003/0048453 A1* | 3/2003 | Mori et al. | 356/445 |
| 2003/0224370 A1* | 12/2003 | Rassman et al. | 435/6 |
| 2006/0072113 A1* | 4/2006 | Ran et al. | 356/445 |
| 2009/0141376 A1* | 6/2009 | Smith et al. | 359/833 |
| 2009/0168061 A1* | 7/2009 | Haga et al. | 356/317 |
| 2009/0245604 A1* | 10/2009 | Maekawa et al. | 382/128 |

FOREIGN PATENT DOCUMENTS

JP    2006-153639    6/2006

OTHER PUBLICATIONS

Braslavsky, Ido et al., "Sequence information can be obtained from single DNA molecules," PNAS 2003, vol. 100, No. 7, pp. 3960-3964.

(Continued)

*Primary Examiner* — David Porta
*Assistant Examiner* — Casey Bryant
(74) *Attorney, Agent, or Firm* — McDermott Will & Emery LLP

(57) ABSTRACT

The present invention aims at reducing background noise derived from a substance that is present in the vicinity of a target substance such as a DNA and protein and attached to the surface of a substrate without an effect on a fluorescent dye labeling the target substance. The substrate that has a probe and is capable of interacting with the target substance is irradiated with noise removing light such that an evanescent field is generated on the surface of the substrate. A target substance and a foreign particle, which are non-specifically stuck to the surface of the substrate, are decomposed by the evanescent field generated by the irradiation with the noise removing light. The evanescent field present near the surface of the substrate has almost no effect on the probe. It is possible to reduce the background noise derived from the substance that is present in the vicinity of the target substance and attached to the surface of the substrate and suppress effects on the probe and the target substance interacting with the probe.

11 Claims, 7 Drawing Sheets

OTHER PUBLICATIONS

Ruparel, Hameer et al., "Design and synthesis of a 3'-O-allyl photocleavable fluorescent nucleotide as a reversible terminator for DNA sequencing by synthesis," PNAS 2005, vol. 102, No. 17, pp. 5932-5937.

Axelrod, Daniel et al., "Total Internal Reflection Fluorescence Microscopy Interactive Java Tutorials Evanescent Field Penetration Depth," (online) Olympus America Inc., retrieve Feb. 24, 2009. <URL:http://www.olympusmicro.com/primer/java/tirf/penetration/index.html>.

Foquet, Mathieu et al., "Improved fabrication of zero-mode waveguides for single-molecule detection," Journal of Applied Physics 2008, vol. 103, 034301.

"Optical Cleaning," Optical Application Technology, Material Encyclopedia, Chapter 2, Section 1, p. 8, Sangyo Gijutsu Service Center.

* cited by examiner

METHOD FOR FLUORESCENCE ANALYSIS AND FLUORESCENCE ANALYZER

BACKGROUND OF THE INVENTION

1. Field of the Invention

The present invention relates to a technique for fluorescence analysis, and more particularly to a technique for improving a signal-to-noise ratio in detection of faint fluorescence emitted by a single molecule or of faint fluorescence emitted by a small number of molecules.

2. Description of the Related Art

In order to detect a target substance such as a deoxyribonucleic acid (DNA) and a protein, the following method has been widely used. That is, a target substance is fluorescently labeled and irradiated with predetermined excitation light such as a laser beam, and fluorescence generated by the irradiation is detected. As a nucleic acid analysis device, a new technique for determining a base sequence of a DNA and a base sequence of a ribonucleic acid (RNA) has been developed.

In a method using electrophoresis that is typically used, a reverse transcription reaction is performed on a DNA fragment or an RNA sample, which is used to determine a sequence, to prepare a synthesized complementary DNA (cDNA) fragment sample; a dideoxy reaction is performed through a known Sanger method; the electrophoresis is performed; and a molecular weight separation and a molecular weight distribution are measured and analyzed.

In recent years, as disclosed in "P.N.A.S. 2003, Vol. 100, pp. 3960-3964" (Non-Patent Document 1), a method for fixing a DNA or the like to a substrate and determining a base sequence of the DNA or the like has been proposed. This method is generally called "sequencing by synthesis". In this method, sample DNA pieces to be analyzed are randomly captured by the surface of the substrate on a molecule basis; bases are elongated on a single base basis or on a several-base basis; and the results of the elongations are detected through a fluorescence measurement to determine a base sequence. In this method, there is a possibility that the base sequence can be determined for each DNA molecule. Therefore, it may be unnecessary that a sample DNA be purified and amplified by cloning, a polymerase chain reaction (PCR) or the like. Therefore, it can be expected that a genomic analysis and a genetic diagnosis are accelerated. In Non-Patent Document 1, a solution is exchanged for cleaning in order to reduce background noise and improve a signal-to-noise ratio.

In "PNAS 2005, Vol. 102, pp. 5932-5937" (Non-Patent Document 2), a method for determining a DNA sequence using a stepwise elongation reaction is disclosed.

In "Optical Application Technology, Material Encyclopedia, Chapter 2, Section 1, Page 8, "Optical cleaning", Sangyo Gijutsu Service Center" (Non-Patent Document 3), photocleaning by ultraviolet excimer lamps is disclosed as a cleaning method used in another technical field. The photo-cleaning by ultraviolet excimer lamps is performed for an organic substance attached to the surface of a substrate in a process of manufacturing a liquid crystal panel. Light, which is emitted by an excimer lamp and has a wavelength of approximately 172 nm, has photon energy larger than bonding energy of a large number of covalent bonds present in the organic substance. The organic substance is therefore decomposed and vaporized, and the surface of the substance can be cleaned.

In a method disclosed in JP-A-2006-153639 (Patent Document 1), a region present on a substrate, in which a probe is not present, is irradiated with light to eliminate fluorescence emitted by a fluorescent dye that is not captured by a probe.

In U.S. Pat. No. 7,329,492 (Patent Document 2), a method for determining a DNA sequence is disclosed. In the method, an enzyme is fixed to a substrate, and the DNA sequence is determined using fluorescence resonance energy transfer (FRET).

Non-Patent Document 4 "Daniel Axelrod et al. 'Total Internal Reflection Fluorescence Microscopy Interactive Java Tutorials Evanescent Field Penetration Depth'. [online]. Olympus America Inc. [retrieved on 2009-02-24]. Retrieved from the Internet: <URL: http://www.olympusmicro.com/primer/java/tirf/penetration/index.html>." describes about evanescent light. An electromagnetic wave (light) having a wavelength of $\lambda$ is incident on an interface between an incident-side medium having a refractive index of n1 and an outgoing-side medium having a refractive index n2 at an incident angle of $\theta$. In this case, the following expression is established: $\theta c = \sin^{-1}(n2/n1)$. The symbol $\theta c$ is called a critical angle ($\sin^{-1}$ is an inverse function of sine). When the incident angle $\theta$ is equal to or larger than the critical angle $\theta c$, the electromagnetic wave is totally reflected by the interface between the incident-side medium and the outgoing-side medium. In this case, an electromagnetic field is generated on the side of the outgoing-side medium with respect to the interface. The intensity of the electromagnetic field is reduced exponentially with distance from the interface. The electromagnetic field is called an evanescent field (light). A relative intensity (E) of the evanescent field is a function of the distance (z) from the interface. When the evanescent field is present on the interface (z=0), the relative intensity (E) of the evanescent field is 1, which is the maximum value. The relative intensity of the evanescent field is represented by the following formula: $E = \exp(-z/d)$, where d is determined based on the wavelength, the incident angle and the refractive indexes. The value d is called a penetration depth. It is known that the penetration depth d is represented by the following formula: $d = \lambda/(4\pi(n1^2 \times \sin^2\theta - n2^2)^{1/2})$, where n1 is the refractive index of the incident-side medium; n2 is the refractive index of the outgoing-side medium; $\theta$ is the incident angle; and $\lambda$ is the wavelength.

SUMMARY OF THE INVENTION

The present inventors studied detection of faint fluorescence emitted by a single molecule or faint fluorescence emitted by a small number of molecules and obtained the following knowledge.

In general, most of foreign particles (organic substances) emit faint fluorescence. In an analysis of fluorescence emitted by a single molecule or fluorescence emitted by a small number of molecules, even an extremely small amount of foreign particles are treated as severe noise.

In the analysis of fluorescence emitted by a single molecule or fluorescence emitted by a small number of molecules, a fluorescent signal is very weak. Thus, an effect of background noise caused by a causative substance is large. A causative substance (causing noise) of a single molecule or a causative substance (causing noise) of a small number of molecules has a significant effect on the analysis, although the substance does not have a significant effect on a conventional analysis of fluorescence emitted by a large number of molecules. For example, even when a single substance (causing noise) is present, the following two types of light cannot be distinguished: light coming from a target substance captured by a probe; and light coming from the single substance that causes noise and is located in the vicinity of the probe and attached to the surface of a substrate.

In the present application, the background noise means a signal derived from a substance other than a target substance (to be measured) captured by a probe. The causative substance means a substance that causes generation of light that is background noise caused by emission of light (fluorescence) or dispersion of the light. The causative substance is, for example, an organic substance. The causative substance that causes generation of fluorescence having a high intensity includes biological materials (amino acids such as tyrosine and tryptophane, NADH, FAD, proteins such as collagen and elastin, etc.) and dust. In addition, when the target substance to be used for the analysis is not captured by the probe, the target substance is regarded as the causative substance that causes noise. Since those causative substances float in the air and water, they may be mixed into a device in processes such as a process of manufacturing a measurement device, a process of preparing a sample and a measurement process. Some of the causative substances pass through filters since they are very small. It is nearly impossible to suppress the mixing to a level at which the analysis of fluorescence emitted by a single molecule is not affected by the mixing. In addition, since the target substance is required for the analysis, it is impossible to avoid the mixing of the target substance into the device.

It is, therefore, necessary to remove the causative substances present on the surface of the substrate in order to reduce the background noise. However, there has been no conventional technique capable of being used for the fluorescence analysis. In a process of exchanging a solution to perform cleaning, the target substance captured by the probe may be removed from the probe. This is a severe problem to the analysis of fluorescence emitted by a single molecule or fluorescence emitted by a small number of molecules. Furthermore, the exchange of the solution leads to increases in the amount of a reagent required for the analysis and in a time required for the analysis.

In photo-cleaning by ultraviolet excimer lamps method, not only a substance that causes background noise but also a probe DNA may be decomposed. Therefore, the photo-cleaning by ultraviolet excimer lamps method cannot be performed in the fluorescence analysis.

In such a method as described in Patent Document 1 for irradiating with ultraviolet light a region in which a probe DNA is not present, a causative substance (that causes noise) present in the vicinity of the probe DNA cannot be removed. This method does not contribute to a reduction in the background noise.

It is, therefore, an object of the present invention to reduce background noise derived from a causative substance (that causes noise) that is located in the vicinity of a target substance such as a DNA and protein and attached to the surface of a substrate without an effect on a fluorescent dye labeling the target substance.

The present invention provides a technique for irradiating a substrate having a probe capable of interacting with a target substance with noise removing light such that an evanescent field is generated on the surface of the substrate. A target substance and a foreign particle, which are non-specifically stuck to the surface of the substrate, are decomposed by the evanescent field generated by the irradiation with the noise removing light. The evanescent field present near the surface of the substrate has almost no effect on the probe.

According to the present invention, background noise derived from a causative substance that is located near a probe and attached to the surface of a substrate is reduced, while effects on the probe and a target substance interacting with the probe can be suppressed.

BRIEF DESCRIPTION OF THE DRAWINGS

Other objects and advantages of the invention will become apparent from the following description of embodiments with reference to the accompanying drawings in which.

DESCRIPTION OF THE PREFERRED EMBODIMENTS

Figure 1:
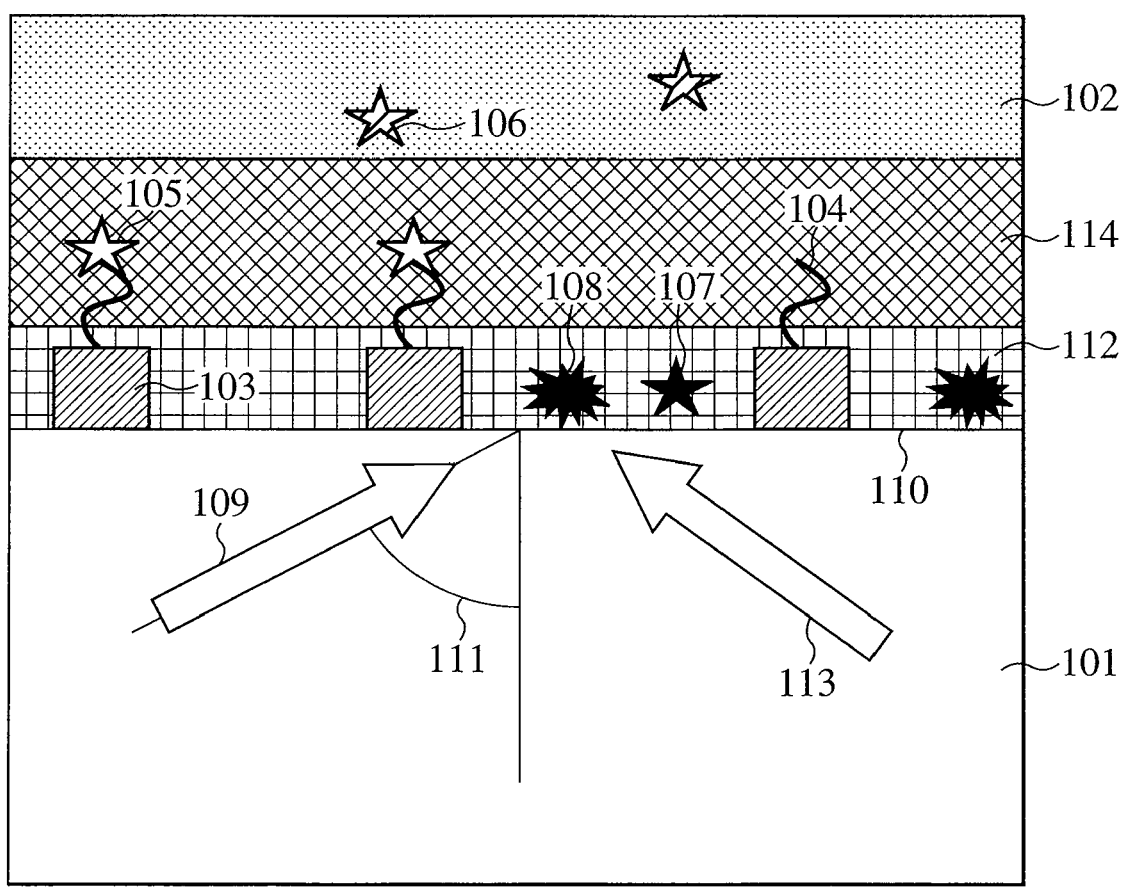
FIG. 1 is a diagram showing the outline of a nucleic acid analysis device.

In a first embodiment (described below) of the present invention, a fluorescence analyzer has: a substrate provided with a probe capable of interacting with a target substance; an excitation light irradiation optical system for irradiating the target substance or the probe with excitation light; a fluorescence detection optical system for detecting fluorescence generated by the irradiation with the excitation light; and a noise removing optical system for irradiating the substrate with noise removing light capable of decomposing the target substance and a foreign particle, which are non-specifically stuck to the surface of the substrate, under a condition that an evanescent field is generated on the surface of the substrate. The probe is present outside the evanescent field.

In another type of the fluorescence analyzer, the excitation light irradiation optical system irradiates the substrate with the excitation light in order that an evanescent field is generated on the surface of the substrate.

In another type of the fluorescence analyzer, a penetration depth of the evanescent field generated by the irradiation with the excitation light is longer than a penetration depth of the evanescent field generated by the irradiation with the noise removing light.

In another type of the fluorescence analyzer, the excitation light is visible light, and the noise removing light is ultraviolet light.

In another type of the fluorescence analyzer, a spacer is present on the surface of the substrate and provided with the probe.

In another type of the fluorescence analyzer, a support body is provided with the probe and faces the surface of the substrate.

In another type of the fluorescence analyzer, the noise removing optical system irradiates the substrate with the noise removing light such that the noise removing light is totally reflected by an interface between the substrate and a solution and an evanescent field is generated on the surface of the substrate.

In another type of the fluorescence analyzer, the substrate has a nano-aperture, and the noise removing optical system irradiates the nano-aperture with the noise removing light such that an evanescent field is generated on the surface of the substrate.

In another type of the fluorescence analyzer, the probe is any one of a deoxyribonucleic acid, a ribonucleic acid, an aptamer, a gene, a nucleosome, a chromatin, a chromosome, a nucleoid, a cell membrane, a cell wall, a virus, an antigen, an antibody, a lectin, a hapten, a receptor, an enzyme, a peptide, a glycosphingolipid and a sphingolipid.

In another type of the fluorescence analyzer, the target substance is any one of a deoxyribonucleic acid, a ribonucleic acid, an adapter, an antigen, an antibody, a deoxyribonucleoside triphosphate, and a ribonucleoside triphosphate.

In another type of the fluorescence analyzer, the target substance is a monomer of a fluorescent-labeled nucleotide or an oligomer of a fluorescent-labeled nucleotide, and the probe is a nucleic acid synthesis enzyme or a nucleic acid molecule. The probe interacts with the target substance to generate a nucleic acid chain containing the nucleotide, and fluorescence emitted by a fluorescent dye contained in the nucleotide is detected to acquire information on a nucleic acid sequence.

In another type of the fluorescence analyzer, the noise removing optical system is capable of irradiating, with the noise removing light, an area that is not irradiated with the excitation light.

Another fluorescence analyzer includes: an optically transparent substrate having a spacer capable of having a probe; a reaction tank capable of holding, on the surface of the optically transparent substrate, a solution containing a target substance capable of interacting with the probe; a prism that is in direct contact with or in indirect contact with the optically transparent substrate; a light source capable of emitting excitation light that is laser light; and a light source capable of emitting ultraviolet light that is laser light, wherein the excitation light is incident on the prism and totally reflected by the surface of the optically transparent substrate to generate an evanescent field in a region in which the probe is present, and the ultraviolet light is incident on the prism and totally reflected by the surface of the optically transparent substrate to generate an evanescent field in a region in which the probe is not present.

Another fluorescence analyzer includes: an optically transparent substrate; a support body facing the surface of the optically transparent substrate and capable of having a probe; a reaction tank capable of holding, on the surface of the optically transparent substrate, a solution containing a target substance capable of interacting with the probe; a prism that is in direct contact with or in indirect contact with the optically transparent substrate; a light source capable of emitting excitation light that is laser light; and a light source capable of emitting ultraviolet light that is laser light, wherein the excitation light is incident on the prism and totally reflected by the surface of the optically transparent substrate to generate an evanescent field in a region in which the probe is present, and the ultraviolet light is incident on the prism and totally reflected by the surface of the optically transparent substrate to generate an evanescent field in a region in which the probe is not present.

Another fluorescence analyzer includes: a spacer capable of having a probe; a substrate having a nano-aperture; a reaction tank capable of holding, on the surface of the optically transparent substrate, a solution containing a target substance capable of interacting with the probe; a light source capable of emitting excitation light that is laser light; and a light source capable of emitting ultraviolet light that is laser light, wherein the nano-aperture is irradiated with the excitation light and an evanescent field is generated in a region in which the probe is present, and the nano-aperture is irradiated with the ultraviolet light and an evanescent field is generated in a region in which the probe is not present.

Another fluorescence analyzer includes: an optically transparent substrate; a support body facing the surface of the optically transparent substrate and capable of having a probe; a spacer capable of having a probe; a substrate having a nano-aperture; a reaction tank capable of holding, on the surface of the substrate, a solution containing a target substance capable of interacting with the probe; a light source capable of emitting excitation light that is laser light; and a light source capable of emitting ultraviolet light that is laser light, wherein the nano-aperture is irradiated with the excitation light and an evanescent field is generated in a region in which the probe is present, and the nano-aperture is irradiated with the ultraviolet light and an evanescent field is generated in a region in which the probe is not present.

Another fluorescence analyzer includes: a substrate having a probe capable of interacting with a target substance; a first reaction tank capable of holding a solution on the surface of the substrate; a noise removing optical system for irradiating the substrate provided in the first reaction tank with noise removing light under a condition that an evanescent field is generated on the surface of the substrate; a second reaction tank capable of holding, on the surface of an optically transparent substrate, a solution containing the target substance capable of interacting with the probe; an excitation light irradiation optical system for irradiating the substrate provided in the second reaction tank with excitation light; and a fluorescence detection optical system for detecting fluorescence generated by the irradiation with the excitation light.

A description will be made of the above fluorescence analyzers, and characteristics and effects of the present invention, with reference to the accompanying drawings. The drawings are used to understand the invention and do not limit the scope of the present invention. Each of the embodiments of the present invention may be combined with the other one or two of the embodiments.

First Embodiment

In the first embodiment of the present invention, a description will be made of a method for removing noise through a fluorescence analysis and an analyzer using the method with reference to FIGS. 1 to 6.

In the present embodiment, a probe 104 is fixed to a device substrate 101 via a spacer 103. A reaction solution 102 is in contact with the substrate 101 and held by the substrate 101. A fluorescent-labeled, unreacted target substance 106 is included in the reaction solution 102. One or more of target substances is specifically captured by the probe 104, and another or other target substances is non-specifically attached to the surface of the substrate 101. A target substance 105 is specifically captured by the probe 104. The target substance 105 is irradiated with excitation light 113 to generate fluorescence. Fluorescence is widely used in a labeling method and in a known detection method. For example, fluorescence is imaged on a two dimensional charge-coupled device and thereby detected by a certain optical system. Noise removing light 109 is incident on an interface 110 between the device substrate 101 and the reaction solution 102 at an incident angle 111 (with respect to a normal to the interface 110) larger than the critical angle and then totally reflected to generate an evanescent field 112 on the side of the reaction solution 102 with respect to the interface 110.

A foreign particle 108, which is not the target substance and causes noise, is attached to the surface of the device substrate for various reasons in general. The foreign particle, which is an organic substance, causes noise due to fluorescence or light dispersion in many cases. In addition, a target substance non-specifically attached to and present on the surface of the device substrate 101 causes noise as described above. It is preferable that only the specifically captured target substance 105 be left and a substance attached to the device substrate be removed. More preferably, effects on the probe 104 and on the unreacted target substance 106 that will react and contribute to generation of a fluorescent signal needs to be suppressed to the minimum level.

A target substance 107 and a foreign particle 108 are non-specifically attached to the surface of the device substrate 101. In the present embodiment, the target substance 107 and the foreign particle 108 are decomposed by energy of the noise removing light. Fluorescence derived from these substances are significantly reduced or eliminated. On the other hand, since a light intensity of the evanescent field generated by the irradiation with the noise removing light can be significantly reduced depending on the distance between the interface 110 (on which the noise removing light 109 is totally reflected) and the probe 104, the specifically captured target substance 105 and the unreacted target substance 106 floating in the reaction solution 102 are not affected by the noise removing light 109. According to the present embodiment, only fluorescence generated from a predetermined target substance can be analyzed.

As the device substrate 101, a material substantially transparent to the noise removing light may be used. Specifically, at least one of plastic, inorganic polymer, metal, natural polymer, and ceramic may be used as the device substrate 101. Polyethylene, polystyrene, polycarbonate, polypropylene, polyamide, phenolic resin, epoxy resin, polycarbodiimide resin, polyvinyl chloride, polyvinylidene fluoride, polytetrafluoroethylene, polyimide and acrylic resin may be used as the plastic. As the inorganic polymer, glass, crystal, carbon, silica gel, and graphite may be used. As the metal, solid metal at ordinary temperatures, such as gold, platinum, silver, copper, iron, aluminum, and magnet, may be used. As the natural polymer and ceramic, diamond, sapphire, alumina, silica, silicon carbide and boron carbide may be used. When the excitation light is emitted from the side of the device substrate, it is desirable that a material substantially transparent to the excitation light be used for the device substrate 101. In order to cause the noise removing light to be totally reflected by the interface 110 between the device substrate 101 and the reaction solution 102 to generate an evanescent field, it is necessary that the material of the device substrate 101 have a larger refractive index to the noise removing light than that of the reaction solution 102. Specifically, it is preferable that a synthetic quartz, a crystal, a sapphire, or an optical glass be used as the device substrate 101.

As the noise removing light 109, various types of light may be used. Ultraviolet light exhibits a high capability to decompose a substance that causes noise. There is a low possibility that light having wavelengths in the visual light range damages the probe and the target substance. For example, photon energy of ultraviolet light having a wavelength of 200 nm or less is relatively high, and is higher than the bond energy of a carbon-carbon double bond, the bond energy of an oxygen-oxygen double bond, the bond energy of a carbon-hydrogen bond, and the bond energy of an oxygen-hydrogen bond and the like. Therefore, the ultraviolet light having a wavelength of 200 nm or less can break most of covalent bonds existing in an organic substance. The photon energy of light having a wavelength of 400 nm or more is lower than the photon energy of the ultraviolet light having a wavelength of 200 nm or less, and is also lower than the bond energy of the carbon-carbon double bond, the bond energy of the oxygen-oxygen double bond, the bond energy of the carbon-hydrogen bond, the bond energy of the oxygen-hydrogen bond, the bond energy of a carbon-carbon bond, the bond energy of a carbon-oxygen bond and the like. The carbon-carbon bond and the carbon-oxygen bond are relatively unstable. Therefore, there is a lower possibility that the light having a wavelength of 400 nm or more damages the probe and the target substance. The light having a wavelength of 400 nm or more has a small effect on direct decomposition of a substance that causes noise, but is absorbed by the substance causing noise and excites the substance, and is therefore capable of improving reactivity of the substance that causes noise. The light having a wavelength of 400 nm or more can indirectly decompose the substance that causes noise. It is preferable that light having high energy, such as a laser beam, be used to more efficiently decompose a substance that causes noise.

The wavelength of the excitation light 113, and the method for the irradiation with the excitation light 113, are not limited as long as the excitation light 113 is capable of exciting a fluorescent body of the target substance. An evanescent field 114 is generated by irradiation of the interface 110 with the excitation light 113 under the condition that the excitation light 113 is totally reflected by the interface 110. The evanescent field 114 may be used to excite the fluorescent body. The evanescent field 114 can suppress fluorescence generated by the unreacted target substance 106 contained in the reaction solution.

The unreacted target substance 106 is not limited as long as the unreacted target substance 106 interacts with the probe 104. As the unreacted target substance 106, the following substances may be used: a nucleic acid; a protein; a sugar chain; a lipid; a complex of those substances; and a compound composed of molecules of those substances resulting from a chemical reaction or an enzyme reaction. More specifically, a fluorescent-labeled DNA, a fluorescent-labeled RNA, a fluorescent-labeled aptamer, a fluorescent-labeled antigen, a fluorescent-labeled antibody, a fluorescent-labeled deoxyribonucleoside triphosphate (used for DNA synthesis), a fluorescent-labeled ribonucleoside triphosphate (used for RNA synthesis) and the like may be used as the unreacted target substance 106. A fluorescent body used for labeling is not limited as long as the fluorescent body is an atom group that emits fluorescence.

The probe 104 is not limited as long as the probe 104 interacts with the unreacted target substance 106. As the probe 104, a nucleic acid, a protein, a sugar chain, a lipid and a complex of those substances may be used. More specifically, the following may be used as the probe 104: a DNA, an RNA, an aptamer, a gene, a nucleosome, a chromatin, a chromosome, a nucleoid, a cell membrane, a cell wall, a virus, an antigen, an antibody, a lectin, a hapten, a receptor, an enzyme, a peptide, a sphingolipid and a glycosphingolipid.

For example, when the fluorescent-labeled deoxyribonucleoside triphosphate is used as the unreacted target substance 106, it is preferable that the probe 104 be a single strand template DNA (to be analyzed), or a complex of the single strand template DNA and oligonucleotide having a complementary sequence, or a complex of the single strand template DNA, the oligonucleotide having a complementary sequence and DNA synthetase.

When the probe 104 has a fluorescent body serving as a donor, fluorescence resonance energy transfer (FRET) can occur. In this case, the unreacted target substance 106 serves as an acceptor. However, the unreacted target substance 106 may serve as a donor and the fluorescent body of the probe 104 may serve as an acceptor.

In addition, it is preferable that the probe 104 used in a nucleic acid analyzer be capable of specifically recognizing and capturing a nucleic acid to be measured. As the probe 104 used in the nucleic acid analyzer, a DNA and an enzyme may be used. For example, when a DNA having an internal sequence with thymines arranged in series is used, an RNA having a poly(A) sequence can be captured by the probe 104. When a DNA polymerase or an RNA polymerase, which allows a nucleic acid to be captured by the probe and synthesized, is used, the nucleic acid can be synthesized on the probe 104. A substrate incorporated in the synthesized nucleic acid during the synthesis is labeled with a fluorescent body and detected. Based on the detection, the sequence of the nucleic acid can be analyzed.

Figure 2:
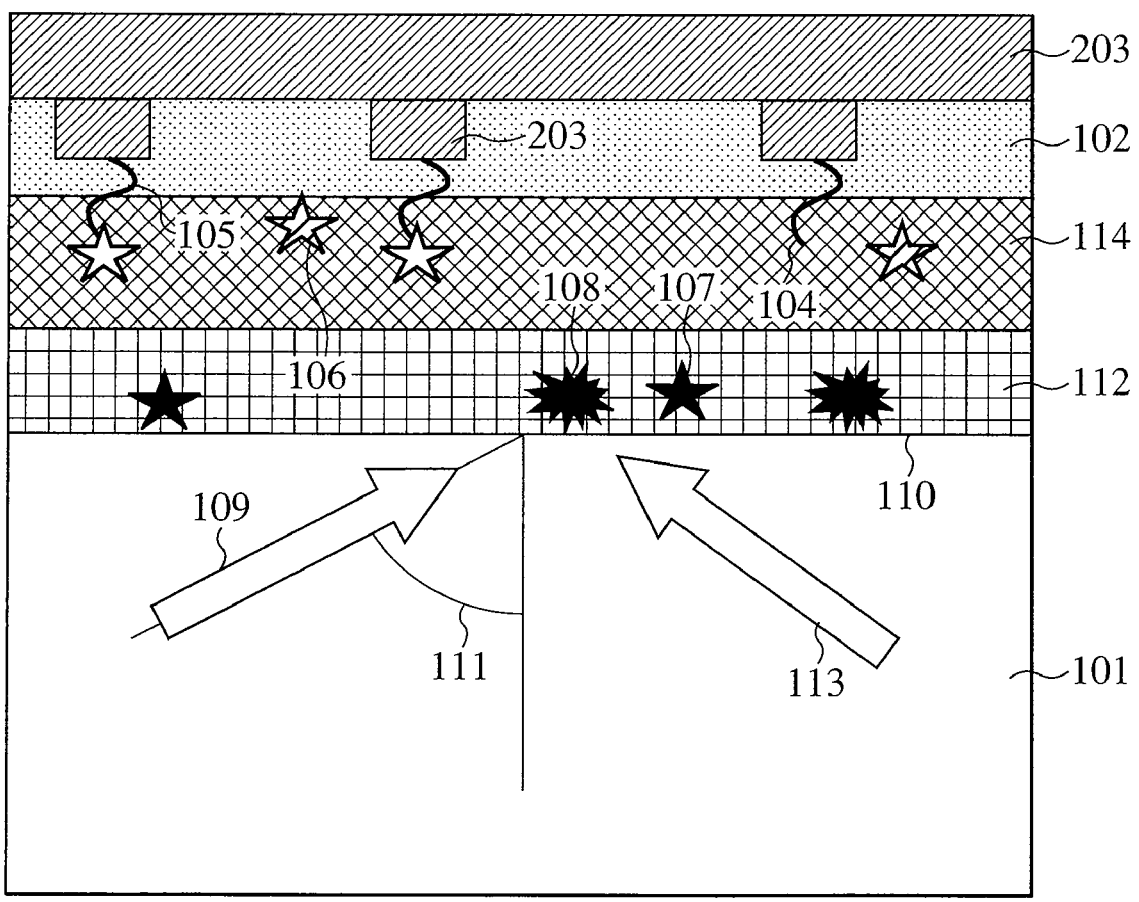
FIG. 2 is a diagram showing a first modified example of the nucleic acid analysis device.

The shape and material of the spacer 103 is not limited as long as the spacer 103 maintains a distance between the surface of the device substrate 101 and the probe 104 and a distance between the surface of the device substrate 101 and the captured target substance 105. Metal, resin, optical glass, quartz and the like may be used for the material of the spacer 103. As shown in FIG. 2, a support body 203 that is not located on the surface of the substrate may be used, and the probe 104 may be fixed to the support body 203, to maintain the distance between the surface of the device substrate 101 and the probe 104 and the distance between the surface of the device substrate 101 and the captured target substance 105. As the support body 203, a surface of the support body 203 facing the surface of the device substrate 101, a side surface of the support body 203, a structure fixed to any of the surfaces and the like may be used. The spacer 103 may be provided for the single probe 104 as shown in FIG. 1. Alternatively, the spacer 103 may be provided for a plurality of probes 104. In addition, a unified spacer 103 may be provided for all probes 104.

Figure 3:
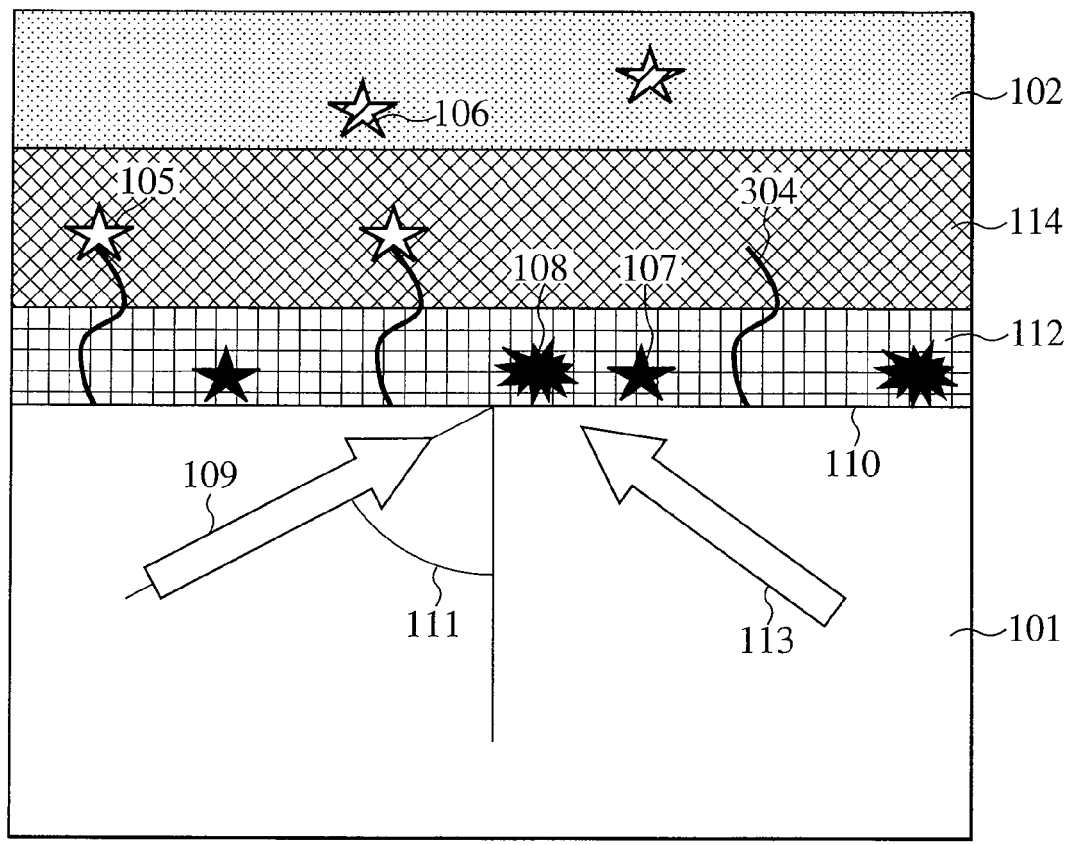
FIG. 3 is a diagram showing a second modified example of the nucleic acid analysis device.

As shown in FIG. 3, a unified spacer probe 304 may be provided. In this case, the spacer probe 304 is not limited as long as the spacer probe 304 has a function for maintaining a distance between the device substrate 101 and the captured target substance 105 and a function for interacting with the target substance 105. In this case, it is preferable that the spacer probe 304 is a DNA having two chains that serve a spacer function and one chain that serves a probe function (located at an end portion of the spacer probe 304). In addition, it is also preferable that a metal structure be used as the spacer probe 304. In this case, when the target substance 105 has a SH group, the spacer probe 304 can be easily fixed.

Furthermore, the spacer 103 may have a sandwich structure or a metal structure made of an appropriate material and having an appropriate shape such as a quadrangular pyramid. In this case, fluorescent enhancement due to localized surface plasmon generated from the structure can be used to reduce background noise derived from fluorescence emitted by the unreacted target substance 106 present in the reaction solution 102. The metal structure can be formed by the following method. That is, a thin film is formed by deposition, sputtering, or deposition and sputtering through a mask, and dry etching or wet etching is then performed on the formed thin film. Alternatively, metal, an insulating material and metal may be continuously deposited and/or subjected to sputtering to form a film, and etching or the like may be performed on the formed film to obtain a desired shape, in order to form the metal structure. Furthermore, metal, an insulating material and metal may be laminated by deposition and/or sputtering through a mask in order to form the metal structure. Alternatively, the following method may be performed to form the metal structure. That is, a metal foil is sandwiched between insulating materials and bonded with the insulating materials. Then, a smooth substrate is bonded with the laminated structure (the metal foil and the insulating materials). The resultant structure is etched to form a desired laminated metal body. An appropriate size of the metal structure varies depending on the wavelength of light used for irradiation. In other words, a resonant frequency suitable for generation of the surface plasmon depends on the interaction of the light with a group of free electrons present on the surface of the metal structure. When the excitation light is visible light, the width and height of the metal structure are preferably in a range of approximately 30 nm to 1000 nm. However, the width and height of the metal structure are not limited to the above range. Metal used for the metal structure preferably has a large negative permittivity since a large depolarization field (which is an electric field having a phase opposite to that of an electric field generated by the light) generated in the metal due to the electric field generated by the light leads to a strong localized surface plasmon. Specifically, it is desirable that noble metal such as gold, silver and platinum be used as the metal of the metal structure.

It is preferable that the distance between the device substrate 101 and the probe 104 be large since effects of the noise removing light on the probe 104 and on the target substance 105 captured by the probe 104 are small when the distance is large. When the evanescent field 114 is used as the excitation light 113, the evanescent field 114 reduces the intensity of the excitation light 113. It is therefore required to balance the excitation light 113 and the evanescent field 114. Specifically, it is preferable that the distance between the device substrate 101 and the probe 104 be smaller than the penetration depth of the evanescent field 114 generated by the irradiation with the excitation light 113 and larger than the penetration depth of the evanescent field 112 generated by the irradiation with the noise removing light 109.

The penetration depths of the evanescent fields 112 and 114 respectively generated by the irradiation with the two types of light 109 and 113 are determined by the wavelengths of the two types of light 109 and 113, refractive indexes (with respect to the two wavelengths of the light 109 and 113) of the two materials between which the interface is present, and incident angles of the two types of light 109 and 113 (with respect to the normal to the interface). It is therefore necessary that those conditions (the material of the device substrate 101, the distance (defined by the spacer 103) between the device substrate 101 and the probe 104, a solvent of the reaction solution 102, the wavelength and incident angle of the noise removing light 109, and the wavelength and incident angle of the excitation light 113) be determined based on the interrelationships between those conditions. Here, it is assumed that refractive indexes of synthetic quartz with respect to light having a wavelength of 193 nm and light having a wavelength of 532 nm are 1.56 and 1.46, respectively. In addition, it is assumed that refractive indexes of water with respect to the light having the wavelength of 193 nm and the light having the wavelength of 532 nm are 1.44 and 1.33, respectively. It is assumed that the interface between the synthetic quartz and the water is irradiated with the light from the side of the synthetic quartz. When the light having the wavelength of 193 nm is incident as the noise removing light 109 on the interface between the synthetic quartz and the water at an incident angle (larger than the critical angle) of 75 degrees with respect to a normal to the interface between the synthetic quartz and the water, the penetration depth of the evanescent field 112 generated on the side of the solution (water) with respect to the interface by the incidence of the noise removing light on the interface is 34.3 nm. The intensity of the evanescent field 112 present at a location distant by 100 nm from the surface of the device substrate 101 is approximately 5.4 percent of the intensity of the evanescent field 112 on the surface of the device substrate 101. On the other hand, when the light having the wavelength of 532 nm is incident as the excitation light 113 on the interface between the synthetic quartz and the water at an incident angle (larger than the critical angle) of 65.7 degrees with respect to the normal to the interface between the synthetic quartz and the water, the penetration depth of the evanescent field 114 generated on the side of the solution (water) with respect to the interface by the incidence of the excitation light 113 on the interface is 1019 nm. The intensity of the evanescent field 114 present at the location distant by 100 nm from the surface of the device substrate 101 is approximately 91 percent of the intensity of the evanescent field 114 on the surface of the device substrate 101.

The intensity of the evanescent field 112 at the location distant by 100 nm from the surface of the device substrate 101 is significantly different from the intensity of the evanescent field 114 at the location distant by 100 nm from the surface of the device substrate 101 as described above. Therefore, it is possible to decompose a causative substance (the target substance 107 and the foreign particle 108) that is non-specifically attached to the surface of the device substrate 101 and causes noise, suppress effects of the noise removing light on the probe 104 and the target substance 105 captured by the probe 104 to the minimum level, and obtain a sufficient intensity of fluorescence derived from the target substance 105 captured by the probe 104. When the target substance 105 is composed of a single molecule or a small number (two to several tens) of molecules, it is important to suppress the effects of the noise removing light on the probe 104 and the target substance 105 captured by the probe 104. This results from the following fact. That is, when the target substance 105 is composed of a large number of molecules, decomposition of the probe 104 and the target substance 105 (captured by the probe 104) due to the effects of the noise removing light only reduces the intensity of fluorescence derived from the target substance 105. However, when the target substance 105 is composed of a single molecule, decomposition of the probe 104 and the target substance 105 (captured by the probe 104) due to the effects of the noise removing light not only reduces the intensity of fluorescence derived from the target substance 105 but also eliminates a fluorescence signal.

For example, when a time constant for extinguishment of light (having a certain intensity) emitted by certain fluorescent molecules is 1 second, light of 90 percent of the fluorescent molecules is extinguished after 2.3 seconds (=1 second× $\log_e 10$). When the number of the fluorescent molecules is approximately 10, light emitted by all the fluorescent molecules is extinguished in many cases after 2.3 seconds.

Figure 4:
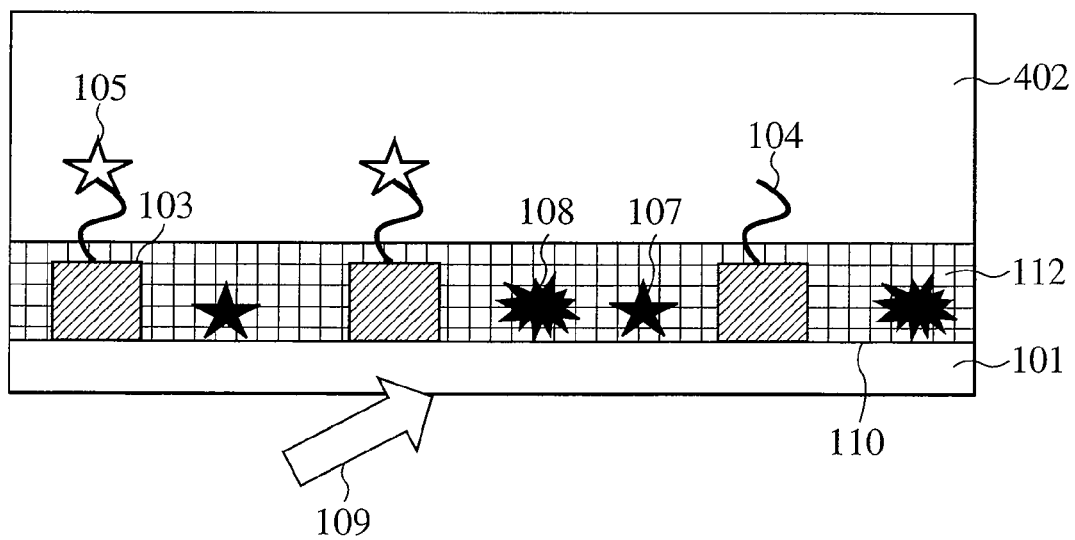
FIG. 4 is a diagram showing the outline of a method for analyzing a nucleic acid.

As shown in FIG. 4, the irradiation with the noise removing light 109 may be performed under the condition that the reaction solution 102 is removed and a space located on and above the device substrate 101 is filled with a medium 402 not containing a fluorescent dye. In this case, the medium 402 may have different refractive indexes to the noise removing light 109 and to the excitation light 113 from those of the reaction solution 102. The degree of freedom of combination of the refractive indexes, wavelengths and incident angles can be increased. Specifically, the medium 402 may be a gas such as air or a liquid such as water. A refractive index of air is smaller than that of water. When the medium 402 is air, the critical angle with respect to the noise removing light 109 can be reduced. Therefore, the noise removing light 109 can be incident on the interface between the device substrate 101 and the medium 402 at a smaller incident angle. In addition, when the noise removing light 109 is incident at the same incident angle as that in the above case on the interface between the device substrate 101 and the medium 402 having a higher refractive index than that of the air, the penetration depth of an evanescent field generated by the incidence of the noise removing light 109 on the interface can be reduced.

Figure 5:
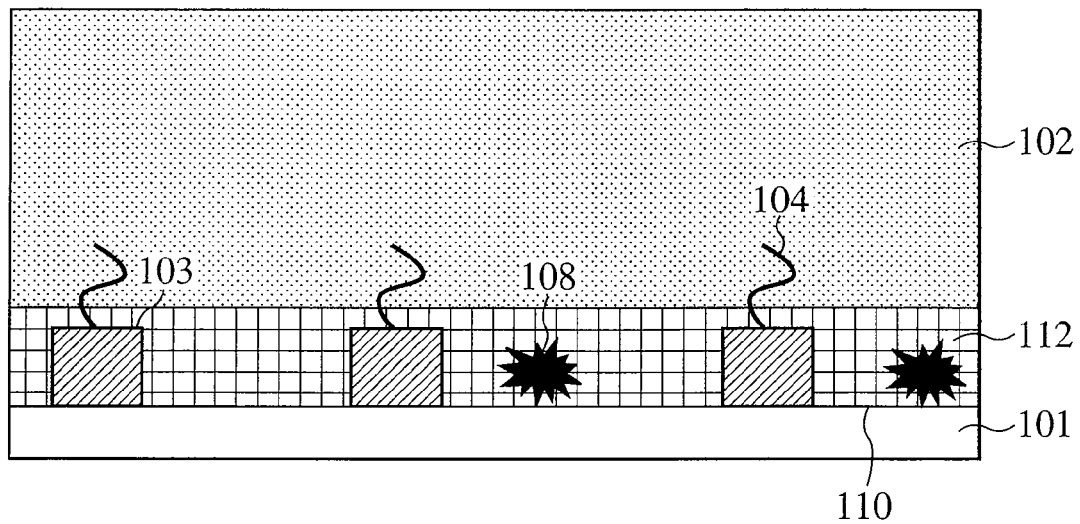
FIG. 5 is a diagram showing a modified example of the nucleic acid analysis device.

As shown in FIG. 5, the irradiation with the noise removing light 109 on the surface of the device substrate 101 may be performed before the unreacted target substance 106 and the reaction solution 102 are introduced. In this case, a causative substance that causes noise is attached to and present on the surface of the device substrate 101 in a manufacturing process, a transfer process, a process of fixing the probe 104 and the like. The causative substance that causes noise can be decomposed by the evanescent field 112 generated by the irradiation with the noise removing light. In this case, it is possible to accomplish the object of the present invention without damaging the probe 104 according to the present embodiment. Even when the irradiation with the noise removing light 109 is performed before the probe 104 is fixed to the device substrate 101 via the spacer 103, noise for the fluorescence analysis can be reduced by decomposing and removing a substance that causes noise. In addition, when the irradiation with the noise removing light is performed before the unreacted target substance 106 and the reaction solution are introduced and before the probe 104 is fixed to the device substrate 101 via the spacer 103, the medium 402 different from the reaction solution 102 used for the fluorescence detection may be used.

After the irradiation with the noise removing light is performed before the unreacted target substance 106 and the reaction solution 102 are introduced and before the probe 104 is fixed to the device substrate 101 via the spacer 103, irradiation with the noise removing light after the reaction solution 102 and the unreacted target substance 106 are introduced may be performed, as shown in FIGS. 1 and 3. The timing for the irradiation with the noise removing light may be the same as the timing for the irradiation with the excitation light for detection of fluorescence. Alternatively, the irradiation with the excitation light may be performed after the irradiation with the noise removing light. When the irradiation with the noise removing light and the irradiation with the excitation light are simultaneously performed, a process between the noise removal and the detection of the fluorescence can be removed. The analyzer can be simplified, and the throughput of the analyzer can be improved. In the case where the irradiation with the excitation light is performed after the irradiation with the noise removing light, a large number of device substrates 101 are simultaneously irradiated with the noise removing light, and subjected to fluorescence detection one by one before the irradiation with the excitation light. In this case, the throughput can be improved, compared with the case where the device substrates 101 are irradiated with the noise removing light one by one.

Figure 6:
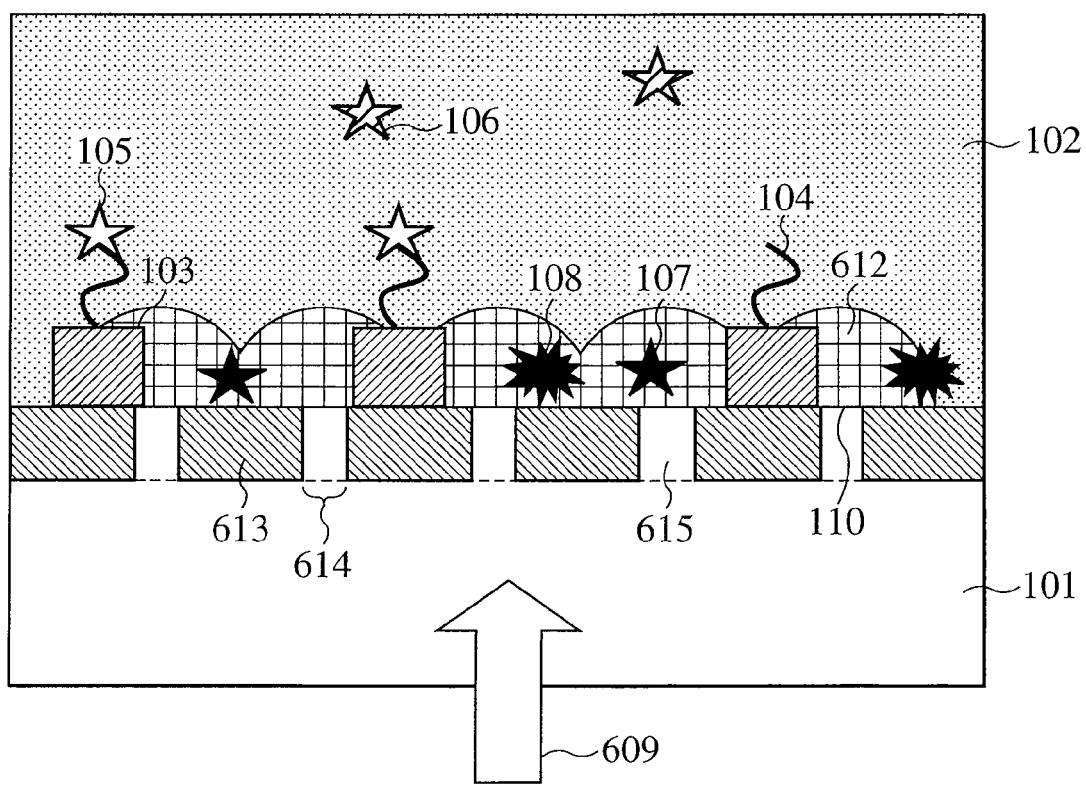
FIG. 6 is a diagram showing a third modified example of the nucleic acid analysis device.

FIG. 6 shows a method for generating an evanescent field 612 through nano-apertures 614 by irradiation of noise removing light 609. A thin light shielding film 613 is provided on the surface of the device substrate 101 on the side of the reaction solution 102. The thin light shielding film 613 shields the noise removing light 609. The nano-apertures 614 are provided in the thin light shielding film 613. The diameter of each of the nano-apertures 614 is smaller than the wavelength of the noise removing light 609. Each of the nano-apertures 614 is filled with a transparent medium 615. The transparent medium 615 is substantially transparent with respect to the noise removing light 609. A material of the transparent medium 615 may be the same as that of the reaction solution 102 or that of the device substrate 101. It is preferable that quartz, sapphire, optical glass and the like be used as the material of the transparent medium 615.

The nano-apertures 614 are formed in the following process. First, aluminum is deposited on the surface of the device substrate 101 to form the thin light shielding film 613 having a thickness of 200 nm. Silver, gold, chrome, silicon carbide and the like may be used to form the thin light shielding film 613 as a substance other than aluminum. The plurality of nano-apertures 614 are formed in the thin light shielding film 613 at an interval of 1 µm by using an electron beam lithography technique. The diameter of each of the nano-apertures 614 is 50 nm. The nano-apertures 614 may extend through the thin light shielding film 613. Alternatively, each of the nano-apertures 614 may be formed such that a portion of the thin light shielding film 613, which is located at the bottom of the nano-aperture 614, remains on the surface of the device substrate 101. A method disclosed in "J. Appl. Phys. 2008, Vol. 103, 034301" may be used to form the nano-apertures 614.

Second Embodiment

In the second embodiment of the present invention, a nucleic acid analyzer, which is suitable for use of the method for removing noise according to the first embodiment, is described with reference to FIGS. 7 to 8F. Points different from the first embodiment are mainly described below.

The nucleic acid analyzer according to the second embodiment has: a section for supplying, to a nucleic acid analysis device, a nucleic acid sample, nucleic acid synthetase and nucleotide containing a fluorescent dye; a section for irradiating the nucleic acid analysis device with light; a light detector for measuring fluorescence emitted by a fluorescent dye incorporated in a nucleic acid chain due to a nucleic acid elongation reaction occurring due to coexistence of the nucleotide, the nucleic acid synthetase and the nucleic acid sample in the nucleic acid analysis device.

Figure 7:
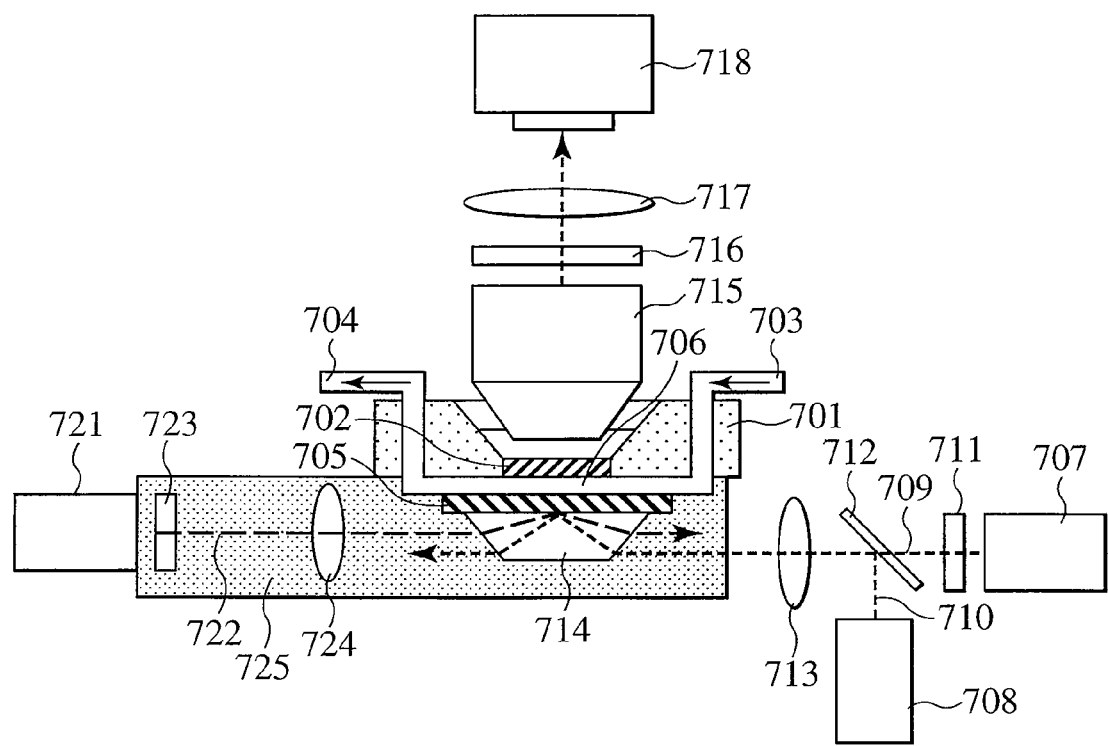
FIG. 7 is a diagram showing the outline of a nucleic acid analyzer.

Referring to FIG. 7, reference numeral 705 denotes the nucleic acid analysis device according to the second embodiment. In the nucleic acid analysis device 705, a metal structure having a height of 100 nm is arranged as the spacer 103 on the surface of the device substrate 101 made of synthetic quartz (made by SHIGUMA KOKI CO., LTD., and having a refractive index of 1.561 to ultraviolet light having a wavelength of 193 nm and a refractive index of 1.45 to 1.48 to light having a wavelength of 350 to 700 nm). In the nucleic acid analysis device 705, a biotin-avidin-biotin-labeled single strand template DNA complex is formed as the probe 104 and fixed to the spacer 103. The formation of the complex serving as the probe 104 and the method for fixing the probe 104 to the spacer 103 are described later.

In the present embodiment, the nucleic acid analysis device 705 is provided in a reaction chamber. The reaction chamber is constituted by a cover plate 701, a detection window 702, a flow path 703 and an outlet 704. The flow path 703 and the outlet 704 serve to exchange a solution. Polydimethylsiloxane (PDMS) is used as a material of the cover plate 701 and a material of the detection window 702. The thickness of the detection window 702 is 0.17 mm. A YAG laser light source (that emits a laser beam having a wavelength of 532 nm and delivers output power of 20 mW) 707 emits a laser beam 709. A YAG laser light source (that emits a laser beam having a wavelength of 355 nm and delivers output power of 20 mW) 708 emits a laser beam 710. A λ/4 plate 711 circularly polarizes only the laser beam 709. A dichroic mirror (that reflects light having a wavelength of 410 nm or less) 712 causes the laser beams 709 and 710 to propagate along the same axis. After that, a lens 713 collects the laser beams 709 and 710. Then, the laser beams 709 and 710 are incident on a prism 714. The laser beams 709 and 710 are then incident on the nucleic acid analysis device 705 at an incident angle (larger than the critical angle) with respect to a normal to the surface of the device 705. According to the present embodiment, an evanescent field is generated on the surface of the device 705 by irradiation with the laser beams emitted by the YAG laser light sources 707 and 708. A fluorescent body of a target substance captured by a probe DNA (coupled with the surface of the device 705) is present in the evanescent field derived from the irradiation with the laser beams emitted by the YAG laser light sources 707 and 708. The fluorescent body is excited by the laser beams 709 and 710. Part of fluorescence emitted from the fluorescent body is output from the detection window 702. The fluorescence output from the detection window 702 is converted into a parallel pencil by an objective lens 715 (having magnification of 60 times, NA of 1.35, and operating distance of 0.15 mm). An optical filter 716 blocks background light and excitation light. Light that passes the optical filter 716 is imaged on a two-dimensional CCD camera 718 by an imaging lens 717.

A noise removing optical system is provided in the apparatus according to the second embodiment as a noise removing light irradiation unit. The noise removing optical system is constituted by the prism 714, and optical parts 721, 723 to 725 as shown in FIG. 7. The optical part 721 is an ArF excimer laser 721 that is an ultraviolet laser light source. The ArF excimer laser 721 (that emits laser light having a wavelength of 193 nm and delivers output power of 30 mV) emits ultraviolet laser light 722 for noise removal. The optical part 724 is a lens 724 that collects the ultraviolet laser light 722. After the lens 724 collects the ultraviolet laser light 722, the ultraviolet laser light 722 is incident on the prism 714. Then, the ultraviolet laser light 722 is incident on the surface of the device 705 at an incident angle of 75 degrees with respect to the normal to the surface of the device 705. The ultraviolet laser light 722 is then totally reflected by the interface between the surface of the device 705 and a solution that is in contact with the surface of the device 705. The optical part 725 is an $N_2$ purge area that includes an optical system for the ultraviolet laser light. A nitrogen gas is present in the $N_2$ purge area 725 to remove oxygen that absorbs ultraviolet light from the optical system. However, an Ar gas may be introduced in the $N_2$ purge area 725. Alternatively, the $N_2$ purge area 725 may be in a vacuum state. In addition, an optical fiber that is made of quartz and has high ultraviolet light transparency or the like may be used as the $N_2$ purge area 725. In this case, the layout of the nucleic acid analyzer is simple since the degree of freedom of the optical path is increased. For the arrangement of the optical parts 721, 723 724 and 725, a general optical system arrangement capable of generating an evanescent field may be used. The layout is not limited as long as the irradiation with the laser light is performed under the condition that the laser light is totally reflected by the interface between the surface of the device 705 and the solution. For example, it is not necessary that the parts 707, 708, and 711 to 714 face each other. The parts 707, 708, and 711 to 714 may be arranged side by side. Alternatively, the surface of each of the parts 707, 708, and 711 to 714 may be perpendicular to the surface of the other one of the parts 707, 708, and 711 to 714. An optical system capable of generating an evanescent field through a nano-aperture may be arranged in the nucleic acid analyzer according to the second embodiment.

According to the present embodiment, an evanescent field is generated on the surface of the device 705 by the irradiation with the ultraviolet laser light. A causative substance that causes noise and is located on the surface of the device 705 is present in the evanescent field derived from the ultraviolet laser light. The probe DNA (provided on the spacer coupled with the surface of the device 705) and the fluorescent body of the target substance (captured by the probe DNA) are present outside the evanescent field derived from the ultraviolet laser light. The causative substance that causes noise can be decomposed by the ultraviolet laser light and the noise is removed, while the probe DNA provided on the spacer and the fluorescent body of the target substance captured by the probe DNA are protected. Therefore, fluorescence can be detected with a high signal-to-noise ratio.

Figure 8A:
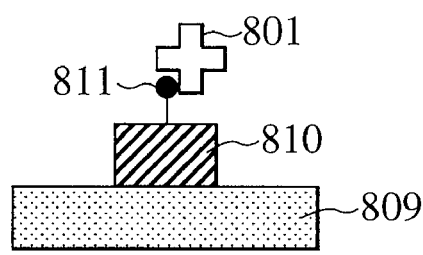
FIG. 8 is a diagram showing the outline of a stepwise elongation reaction.
Figure 8B:
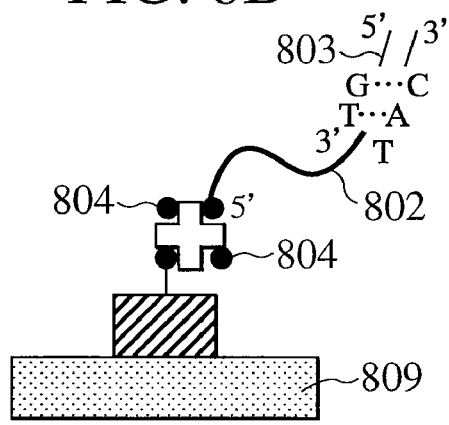
Figure 8C:
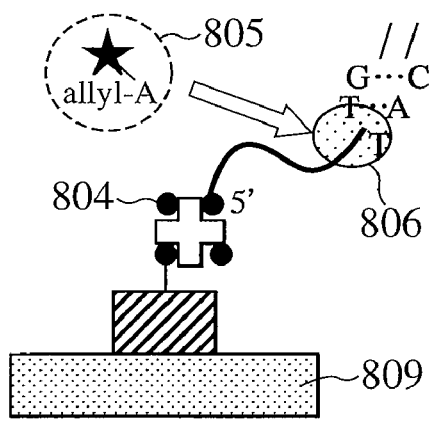
Figure 8D:
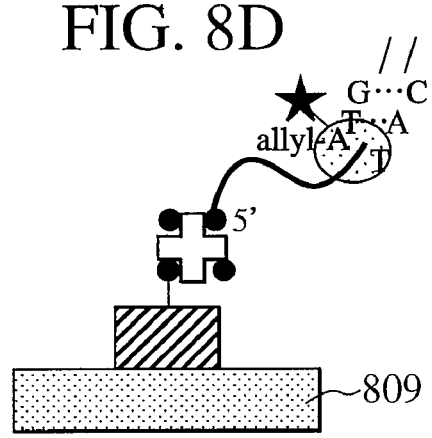
Figure 8E:
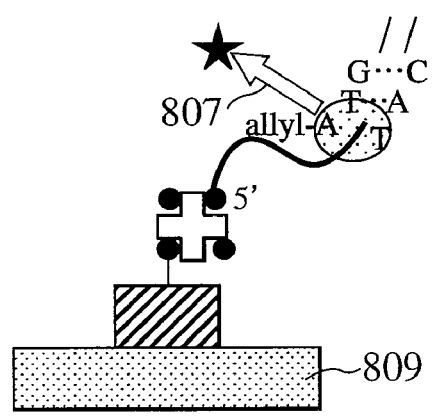
Figure 8F:
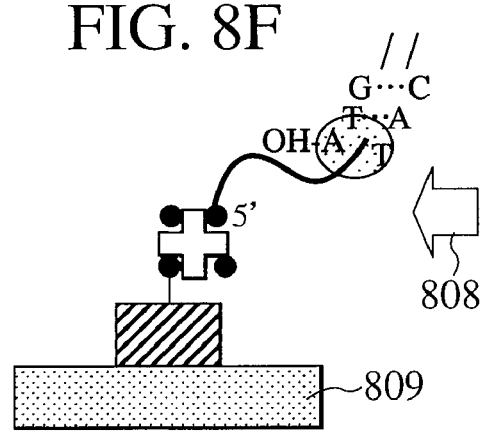

A process of a stepwise elongation reaction is described below with reference to FIGS. 8A to 8F. The reaction process is performed according to Non-Patent Documents 1 and 2. A buffer containing streptavidin 801 is introduced into a reaction tank 706 through the flow path 703. The streptavidin 801 is combined with biotin 811 present on the metal structure 810 of the device 705 to form a biotin-avidin complex (shown in FIG. 8A). A primer 803 is hybridized with a single strand template DNA 802, which is a target modified by biotin. A complex (template DNA-primer complex) of the single strand template DNA and the primer, and a buffer containing an excessive amount of biotin 804, are introduced into the flow path 703 that serves as an inlet. The template DNA-primer complex of a single molecule is fixed through the combination of the biotin and the avidin (shown in FIG. 8B). After the fixation reaction, an excess template DNA-primer complex and excess biotin are rinsed off with a flushing buffer. Then, a Thermo Sequenase reaction buffer (containing Termo Sequenase polymerase 806 and a dATP (3'-O-allyl-dATP-PC-R6G) 805 in which a 3' end labeled with a fluorescent body R6G is modified with an allyl group) is introduced into the reaction tank 706 through the flow path 703. An elongation reaction is then performed. In this case, when a base in a sequence of the single strand template DNA 802, which is located at a position complementary to a position next to a base of the 3' end of the primer 803, is thymine, the dATP 805 is incorporated in the template DNA-primer complex by the polymerase elongation reaction. In addition, since the 3' end of the dATP 805 is modified with the allyl group, one or more bases are not incorporated in the template DNA-primer complex. After the elongation reaction, the unreacted dATP 805 and the polymerase 806 are rinsed off with a flushing buffer from the reaction tank 706. A chip is irradiated with the laser light 709 emitted by the YAG laser light source 707 and fluorescence is detected (FIG. 8D). In this case, it is determined based on the presence of fluorescence at a predetermined location whether or not the dATP is incorporated in the template DNA-primer complex. Then, the chip is irradiated with the laser light 710 emitted by the YAG laser light source 708. A fluorescent body 807, with which the dATP 805 incorporated in the complex is labeled, is removed by photocleavage (FIG. 8E). Then, a solution 808 containing palladium is introduced in the reaction tank 706. The allyl group present at the 3' end of the dATP incorporated in the complex is replaced with a hydroxyl group by a palladium-catalyzed reaction (FIG. 8F). The elongation reaction of the template DNA-primer complex can be carried out again since the allyl group present at the 3' end is replaced with the hydroxyl group. After the palladium-catalyzed reaction, the reaction tank 706 is cleaned with a flushing buffer. The process from a step shown in FIG. 8C to the cleaning is repeatedly performed on each dNTP in the order of ademine (A), cytosine (C), guanine (G), and thymine (T) to determine the sequence of the fixed single strand template DNA 802.

The analyzer according to the present embodiment is capable of measuring fluorescence on a plurality of the metal structures 810 simultaneously. The analyzer is therefore capable of simultaneously determining the types of dNTPs incorporated in template DNA-primer complexes different from each other, i.e., the sequences of template DNAs. When the device according to the present embodiment is used, it is possible to reduce noise derived from the target substance 107 non-specifically stuck onto a device substrate 809. According to the present embodiment, a large number of target substances can be detected at one time with high contrast.

A member other than the device 705 may be irradiated with the noise removing light by means of the noise removing optical system according to the present embodiment. The flow path 703 and the tank (that stores a solution such as a buffer necessary for a reaction) may be irradiated with the noise removing light. This makes it possible to remove noise caused by a substance contained in a buffer or the like. In the analyzer in which the surface of the device 705 is irradiated with the noise removing light, a substance that causes noise and floats in the solution cannot be removed. The irradiation on the flow path 703 or on the tank makes it possible to remove the substance that causes noise and floats in the solution. In this case, when the target substance is decomposed into substances that cause noise, only a solution that does not contain a substance (e.g., the unreacted target substance 106 and the template DNA) having an effect on the subsequent reaction or an effect on the fluorescence detection may be irradiated with the noise removing light. This prevents the effect on the fluorescence detection.

Third Embodiment

Figure 9A:
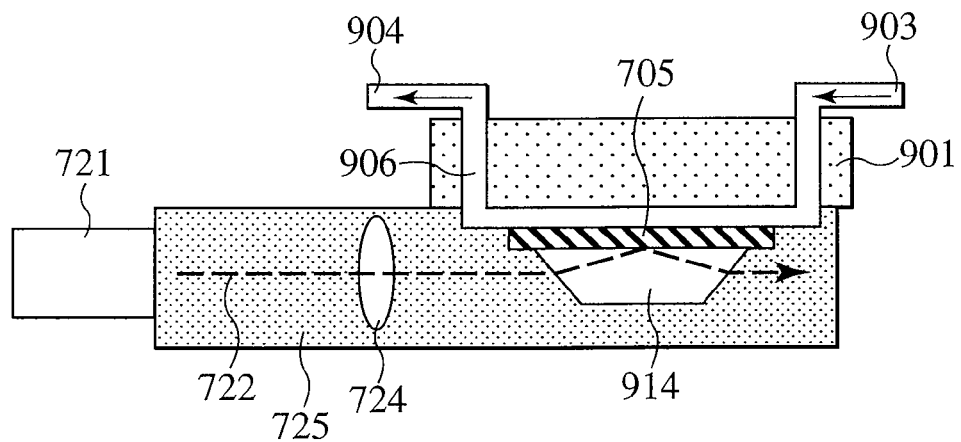
FIG. 9A is a diagram showing the outline of a noise removal device.

Another example of a desired configuration of the nucleic acid analyzer will be described with reference to FIGS. 9A and 9B. Points different from the first and second embodiments will be mainly described.

Figure 9B:
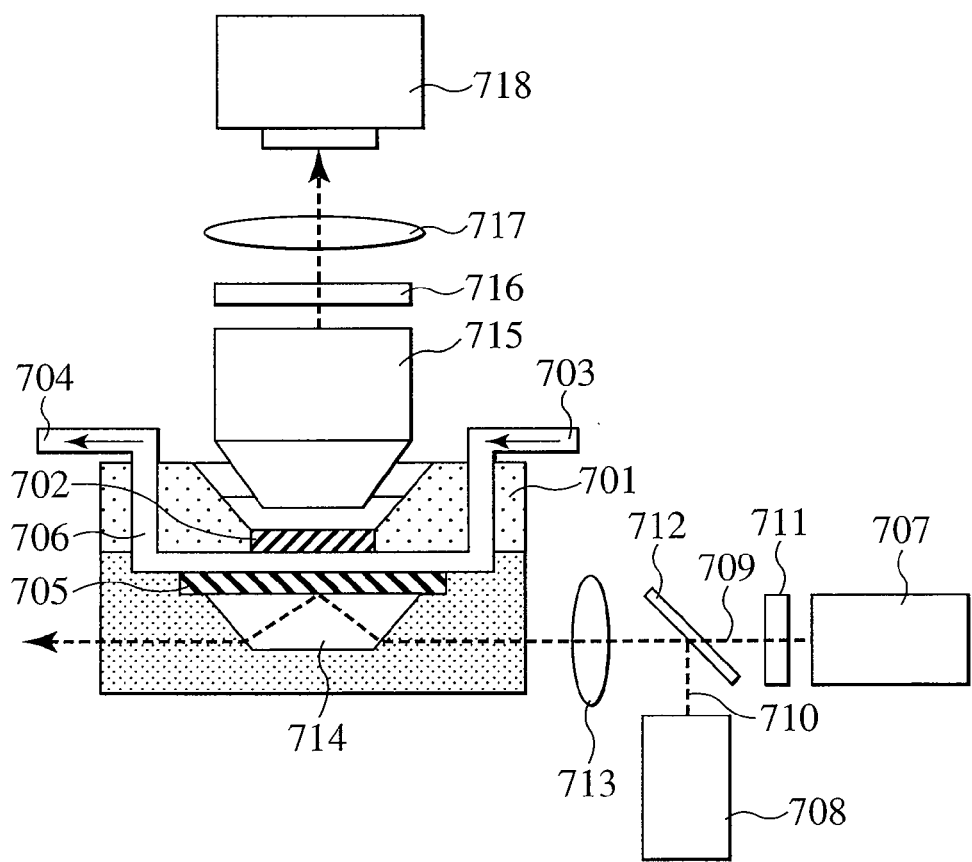
FIG. 9B is a diagram showing the outline of a fluorescence detector.

The nucleic acid analyzer according to the third embodiment of the present invention has a noise removal device (shown in FIG. 9A) and a fluorescence detector (shown in FIG. 9B). First, the noise removal device constituting a part of the analyzer according to the present embodiment will be described.

The device 705 is provided in a noise removal chamber. The noise removal chamber is capable of storing a solution containing a target substance on the side of a low refractive index layer. The noise removal chamber has a cover plate 901, an inlet 903 and an outlet 904. The inlet 903 and the outlet 904 serve to exchange a solution. Parts 721, 723 to 725 provided in the noise removal device, which are shown in FIG. 9A, are substantially the same as the parts 721, 723 to 725, which are shown in FIG. 7. Ultraviolet laser light 722 (shown in FIG. 9A) emitted by the light source 721 is incident on the prism 724 and then incident on the device 705 at an incident angle of 75 degrees with respect to a normal to the surface of the device 705. The ultraviolet laser light 722 is then totally reflected by the interface between the device 705 and a solution (that is in contact with the device 705) to generate an evanescent field 112 on the surface of the device 705. The configuration of the fluorescence detector shown in FIG. 9B is the same as that of a fluorescence analyzer shown in FIG. 7. The fluorescence analyzer shown in FIG. 7 is constituted by parts (other than the noise removing optical system) of the nucleic acid analyzer shown in FIG. 7.

In the present embodiment, the noise removal device has a chamber, and the fluorescence detector has a chamber. However, the chambers and the device 705 may be unified. This means the chamber provided in the noise removal device and the chamber provided in the fluorescence detector are unified.

In the present embodiment, the noise removing optical system and the fluorescence detector are separated from each other. Therefore, it is possible to simultaneously perform irradiation with the noise removing light and detection of fluorescence. In the second embodiment, in order to process a plurality of the devices 705, it is necessary that the irradiation with the noise removing light and the detection of fluorescence be repeatedly performed in this order for the number of the devices 705. In general, a time required for the detection of fluorescence is longer than a time required for the irradiation with the noise removing light. In the present embodiment, it is possible to continuously perform the detection of fluorescence after the irradiation with the noise removing light. Therefore, the throughput of the analyzer is improved. In addition, since the noise removal device holds a plurality of the devices 705, a plurality of the device substrates 101 can be simultaneously irradiated with the noise removing light, and then subjected to fluorescence detection one by one. The throughput can be improved, compared with the case where the device substrates 101 are irradiated with the noise removing light one by one. A medium having a refractive index different from that of the medium present in the reaction tank 706 may be present in the reaction tank 906.

While the invention has been described in its preferred embodiments, it is to be understood that the words which have been used are words of description rather than limitation and that changes within the purview of the appended claims may be made without departing from the true scope and spirit of the invention in its broader aspects.

What is claimed is:

1. A fluorescence analyzer comprising:
a substrate including a probe configured to interact with a target substance;
an excitation light irradiation optical system configured to irradiate the target substance or the probe with excitation light;
a fluorescence detection optical system configured to detect fluorescence generated by the irradiation with the excitation light from the excitation light irradiation optical system; and
a noise removing optical system comprising a noise removing source, wherein the noise removing optical system is configured to irradiate the substrate with noise removing light, wherein the target substance and a foreign particle are non-specifically stuck to the surface of the substrate, and the target substance and the foreign particle are decomposed by the noise removing light, under a condition that an evanescent field is generated on the surface of the substrate, wherein:
the probe is present outside the evanescent field, and inside an area irradiated with excitation light, and
the excitation light irradiation optical system is configured to irradiate the target substance or the probe with excitation light after the noise removing optical system irradiates the substrate with noise removing light.

2. The fluorescence analyzer according to claim 1, wherein the excitation light irradiation optical system is configured to irradiate the substrate with the excitation light, under a condition that an evanescent field is generated on the surface of the substrate.

3. The fluorescence analyzer according to claim 2, wherein the excitation light is visible light, and the noise removing light is ultraviolet light.

4. The fluorescence analyzer according to claim 1, wherein a spacer is present on the surface of the substrate and provided with the probe.

5. The fluorescence analyzer according to claim 1, wherein a support body provided with the probe faces the surface of the substrate.

6. The fluorescence analyzer according to claim 1, wherein the substrate has a nano-aperture, and the noise removing optical system irradiates the nano-aperture with the noise removing light to generate an evanescent field on the surface of the substrate.

7. The fluorescence analyzer according to claim 1, wherein the probe is a deoxyribonucleic acid, a ribonucleic acid, an aptamer, a gene, a nucleosome, a chromatin, a chromosome, a nucleoid, a cell membrane, a cell wall, a virus, an antigen, an antibody, a lectin, a hapten, a receptor, an enzyme, a peptide, a glycosphingolipid or a sphingolipid.

8. The fluorescence analyzer according to claim 1, wherein the target substance is a deoxyribonucleic acid, a ribonucleic acid, an aptamer, an antigen, an antibody, a deoxyribonucleoside triphosphate, or a ribonucleoside triphosphate.

9. The fluorescence analyzer according to claim 1, wherein the target substance is a monomer of a fluorescent-labeled nucleotide or an oligomer of a fluorescent-labeled nucleotide, the probe is a nucleic acid synthesis enzyme or a nucleic acid molecule, the probe interacts with the target substance to generate a nucleic acid chain containing the nucleotide, and fluorescence emitted by a fluorescent dye contained in the nucleotide is detected to acquire information on a nucleic acid sequence.

10. A fluorescence analyzer comprising:
an optically transparent substrate having a spacer comprising a probe;
a reaction tank configured to hold, on the surface of the optically transparent substrate, a solution containing a target substance configured to interact with the probe;
a prism in direct contact with or in indirect contact with the optically transparent substrate;
a first light source configured to emit excitation light that is laser light; and
a noise removing light source configured to emit ultraviolet light that is laser light, wherein:
the excitation light is incident on the prism and totally reflected by the surface of the optically transparent substrate to generate an evanescent field in a region in which the probe is present, and the ultraviolet light is incident on the prism and totally reflected by the surface of the optically transparent substrate to generate an evanescent field in a region in which the probe is not present, and
the first light source is configured to emit the excitation light after the ultraviolet light is emitted.

11. A fluorescence analyzer comprising:
a substrate having a probe configured to interact with a target substance;
a first reaction tank configured to hold a solution on the surface of the substrate;
a noise removing optical system comprising a noise removing source, wherein the noise removing optical system is configured to irradiate the substrate provided in the first reaction tank with a noise removing light, under a condition that an evanescent field is generated on the surface of the substrate;
a second reaction tank configured to hold, on the surface of an optically transparent substrate, a solution containing the target substance capable of interacting with the probe;
an excitation light irradiation optical system configured to irradiating the substrate provided in the second reaction tank with excitation light; and a fluorescence detection optical system configured to detect fluorescence generated by the irradiation with the excitation light,
wherein the excitation light irradiation optical system is configured to irradiate the target substance or the probe with excitation light after the noise removing optical system irradiates the substrate with noise removing light.

* * * * *